United States Patent [19]

Fleury et al.

[11] Patent Number: 5,141,746
[45] Date of Patent: Aug. 25, 1992

[54] PROCESS FOR OBTAINING GENISTIN MALONATE AND DAIDZIN MALONATE

[75] Inventors: Yvette Fleury, Boncourt; Danièle Magnolato, La Tour-de-Peilz, both of Switzerland

[73] Assignee: Nestec S.A., Vevey, Switzerland

[21] Appl. No.: 598,247

[22] Filed: Oct. 16, 1990

[30] Foreign Application Priority Data

Nov. 10, 1989 [CH] Switzerland .......................... 4063/89

[51] Int. Cl.$^5$ ...................... A61K 35/78; A01N 43/04
[52] U.S. Cl. .................................. 424/195.1; 514/25; 549/403; 424/78.03; 426/133
[58] Field of Search ............................ 514/25; 549/403; 424/195.1, 78.03; 426/133

[56] References Cited

U.S. PATENT DOCUMENTS

| | | | |
|---|---|---|---|
| 4,163,746 | 8/1979 | Feuer | 260/345.2 |
| 4,166,862 | 9/1979 | Feuer | 424/263 |
| 4,428,876 | 1/1984 | Iwamura | 260/123.5 |
| 4,524,067 | 6/1985 | Arichi et al. | 514/33 |
| 4,557,927 | 12/1985 | Miyake | 424/48 |
| 4,963,527 | 10/1990 | Bombardelli | 514/25 |

FOREIGN PATENT DOCUMENTS

| | | |
|---|---|---|
| 56-73025 | 1/1981 | Japan . |
| 56-60981 | 3/1981 | Japan . |
| 56-64000 | 3/1981 | Japan . |
| 1-146894 | 6/1989 | Japan . |

*Primary Examiner*—Ronald W. Griffin
*Assistant Examiner*—Ralph Gitomer
*Attorney, Agent, or Firm*—Vogt & O'Donnell

[57] ABSTRACT

Genistin and daidzin malonates are obtained by extracting ground soya bean with methanol or ethanol to obtain an extract. The extract is buffered to a pH of 6 to 9 and then extracted with a water-immiscible solvent. The aqueous phase is recovered, acidified to a pH of 2 to 5.4, and then extracted with a water-immiscible solvent. The organic phase is recovered, neutralized to a pH of 6.8 to 7.2, and the malonates are separated therefrom.

19 Claims, No Drawings

PROCESS FOR OBTAINING GENISTIN MALONATE AND DAIDZIN MALONATE

BACKGROUND OF THE INVENTION

This invention relates to a process for the production of two isoflavones, genistin malonate and daidzin malonate, and to the use of these compounds.

The article of C. M. Francis (J.Sci.Fd Agri.(1973) 24 1235) mentions the presence in clover leaves of genistin malonate, which corresponds to the formula:

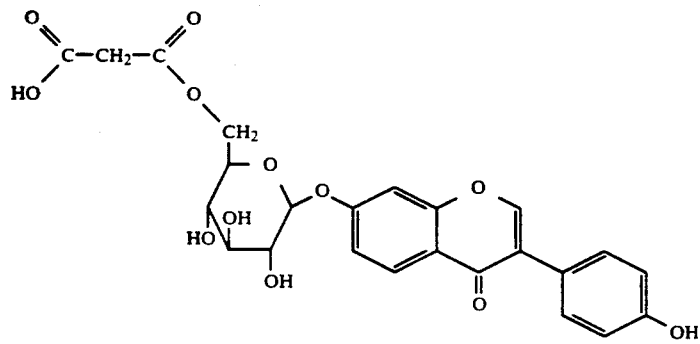

It is also known by Japanese Patent No. 1146894 that daidzin malonate, which corresponds to the formula:

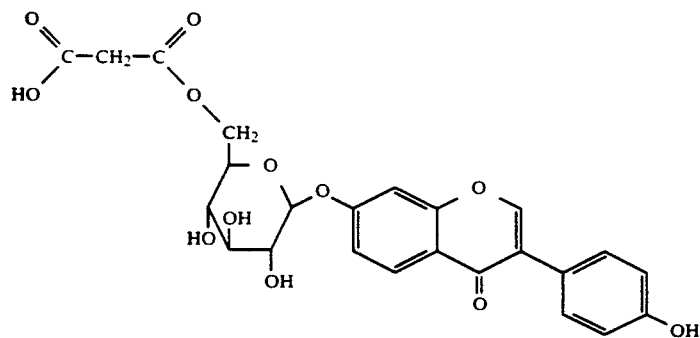

can be extracted from the roots or stems of *Pueraria lobata*.

The object of the present invention is to provide a process for the production of these two isoflavones from an edible raw material, namely soya beans, in a simple and economic way, and with a good yield.

SUMMARY OF THE INVENTION

The process according to the invention is characterized in that ground soya beans are extracted with an alcohol, the crude extract obtained is buffered with an aqueous buffer solution to a pH value of 6-9, the buffer solution containing the crude extract is extracted with a water-immiscible organic solvent, the aqueous phase is recovered and acidified to pH 2.5-4, the acidified aqueous phase is extracted with a water-immiscible organic solvent, the organic phase is recovered and neutralized to pH 6.8-7.2 and the residual compounds are separated.

DETAILED DESCRIPTION OF THE INVENTION

In the process according to the invention, ground soya beans preferably having an average particle diameter of 0.5 to 0.8 mm and a maximum diameter of 1.0 to 1.1 mm may be prepared. Before extraction, the ground soya beans may be defatted to remove from the soya the fats which could subsequently interfere with the correct operation of the process. Defatting may be carried out, for example, by refluxing ground soya beans in an organic solvent, such as hexane or petroleum ether. In one particular embodiment, a mixture containing 1 part by weight ground soya beans to 4-6 parts by weight n-hexane may be heated with stirring (70-90 r.p.m.) for 50-70 minutes at a temperature of 60°-70° C., after which the mixture may be left to cool to room temperature, the ground material may be filtered and then washed with n-hexane and the defatted ground material dried under nitrogen for 10 to 15 hours.

The optionally defatted ground material is then extracted with an alcohol, such as methanol or ethanol for example. This may be done, for example, by refluxing a mixture containing 1 kg defatted ground material and 6 to 8 liters of a 70-90% aqueous methanol solution with stirring (70-90 r.p.m.) for 50-100 minutes at a temperature of 70°-90° C., hot-filtering the mixture and drying the filtrate, for example under reduced pressure in a rotary evaporator at 25°-50° C. A crude extract in the form of a brown-coloured solid can be obtained in this way.

The crude extract is then buffered to bring its pH to a value of 6-9. To this end, the crude extract may be suspended or dissolved in a solution of a weak base, such as an aqueous $NaHCO_3$ solution. This enables the subsequent extraction to be improved, the genistin and the daidzin passing into the organic phase and the desired malonates remaining in the aqueous phase. The buffer solution containing the crude extract is then extracted with a water-immiscible organic solvent, such as butanol or ethyl acetate for example. After extraction, the organic phase mainly contains isoflavones, such as genistin and daidzin, and other constituents while the aqueous phase contains the desired compounds and impurities.

The aqueous phase is acidified to a pH of the order of 2.5–4, for example by addition of concentrated, more particularly 5–10 N, hydrochloric acid. The acidified aqueous phase is extracted with a water-immiscible organic solvent. It is preferred to use a solvent identical with that used for extraction of the aqueous suspension or solution containing the crude extract, i.e. butanol or ethyl acetate, so that there is no need to use several different solvents, which is always dangerous. The organic phase obtained may then be neutralized by adjusting its pH to a value of 6.8–7.2, for example by addition of sodium hydroxide, and dried, for example by evaporation of the solvent under reduced pressure in a rotary evaporator at 25°–50° C. An impure extract containing the desired compounds is thus obtained in the form of a brown-coloured solid.

The residual compounds may then be separated from this extract, for example by adsorption and filtration chromatography of the impure extract, which also enables any impurities, such as the genistin and/or the daidzin still present, to be removed from the extract. This chromatography may be carried out, for example, in a column containing a gel using an alcohol, such as ethanol or a methanol/water mixture, as eluent. Several fractions containing impurities and several fractions containing a mixture of the desired compounds can be obtained. The fractions of interest may then be subjected to a second chromatography to separate the two desired compounds. To this end, inverse-phase chromatography may be carried out using, for example, a polar column containing in particular octadecyl silane groups attached to silica and an eluent or an eluent gradient of decreasing polarity, such as for example a 10–25% solution of methanol, ethanol or acetonitrile. Two fractions each containing a separate compound are obtained in this way. These fractions may be dried, for example in a dry evaporator, under reduced pressure at a temperature of 25° to 50° C. Two compounds are thus obtained in the form of amorphous solids, one pale yellow in colour and the other white in colour, both of which are soluble in polar solvents, such as water, methanol or ethanol.

These two compounds have been found to exhibit remarkable antioxidant properties, being capable of protecting the fats, vitamins and/or oligoelements present in cosmetic or food products against oxidation. Thus, the present invention also includes a method for inhibiting oxidation of a food or cosmetic comprising adding to the food or cosmetic an effective amount of at least one member, and optionally both members, of the group consisting of genistin malonate and daidzin malonate.

EXAMPLES

The present invention is illustrated in more detail by the following preparation example and by the following identification tests for the compounds and activity tests.

EXAMPLE OF PREPARATION OF THE COMPOUNDS i) Defatting 5 kg n-hexane are added to 1 kg ground soya beans having an average particle diameter of 0.8 mm. The mixture is refluxed at a temperature of 65° C. for 1 hour with continuous stirring at 80 r.p.m. This mixture is then left to cool to ambient temperature and filtered, the ground material being recovered and dried under nitrogen for 12 hours. The dry ground material is then mixed with another 5 kg n-hexane and refluxed at 65° C. for 1 hour with continuous stirring. After cooling and filtration, the resulting ground material is washed with 1 liter n-hexane. The ground material is dried under nitrogen for 10 hours. Defatted ground soya beans are thus obtained in a quantity of 0.7 kg.

ii) Preparation of the Crude Extract

A mixture containing 150 g defatted ground soya beans as prepared in step i) and 1 liter of an 80% aqueous methanol solution is prepared. The mixture is refluxed at a temperature of 80° C. for 1 hour with continuous stirring at 80 r.p.m. The mixture is then hot-filtered and the filtrate is retained. The ground material is then heated with stirring for another hour at 80° C. with 1 liter of 80% methanol. The mixture is hot-filtered and the obtained is added to the preceding filtrate. The combined filtrate is evaporated to dryness under reduced pressure in a rotary evaporator at a temperature of 40° C. 32.6 g crude extract in the form of a brown-coloured solid are obtained.

iii) Preparation of the Impure Extract 32.6 g of the crude extract obtained in step ii) are mixed with 150 ml of a 1 M aqueous $NaHCO_3$ solution. 150 ml n-butanol are added, the two phases are mixed and the aqueous phase is recovered by extraction, the butanol phase mainly containing daidzin and genistin. The aqueous phase is acidified to pH 3 by addition of 6.5 N hydrochloric acid. 150 ml n-butanol are added to the aqueous phase and, after mixing, a first organic phase is recovered. Another 150 ml n-butanol are added to the aqueous phase and, after mixing, a second organic phase is recovered.

The pH of the two organic phases are adjusted to 7 by addition of 1 N NaOH and the two phases are dried under reduced pressure in a rotary evaporator at 40° C. Impure extract in the form of a brown-coloured solid is obtained in respective yields of 2.4 g for the first phase and 1.2 g for the second phase.

iv) Separation of the Compounds

A chromatography column containing a gel (Sephadex LH-20) 3 cm in diameter and 50 cm tall is prepared. 2.4 g of the impure extract obtained in step iii) diluted with ethanol is introduced into the column. The impure extract is eluted with ethanol at a rate of 2 ml per minute. A total of 17 fractions are obtained, 6 of these fractions containing the malonates of genistin and daidzin. These 6 fractions are subjected to a second chromatography in a column containing octadecyl silane groups attached to silica (Lobar RP-18). A 10% aqueous ethanol solution is used as the eluent at a rate of 2 ml per minute. Two fractions each containing a different product are finally obtained. These fractions are dried under reduced pressure in an evaporator at a temperature of 40° C. 25 mg daidzin malonate and 80 mg genistin malonate, both highly pure (92–98%), are obtained in the form of amorphous solids, the first white in colour and the second pale yellow in colour.

IDENTIFICATION TESTS FOR THE GENISTIN MALONATE i) Position of the Sugar Group The position of the sugar group having the formula

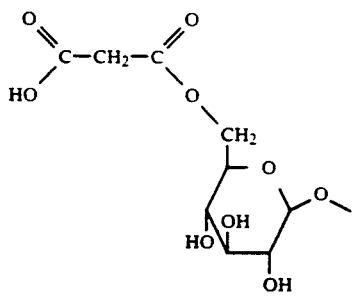

in the genistin malonate molecule is determined by a so-called shift reaction with aluminium chloride.

The free OH group may be in the 5 position or the 7 position, the other position being occupied by the above-mentioned sugar group:

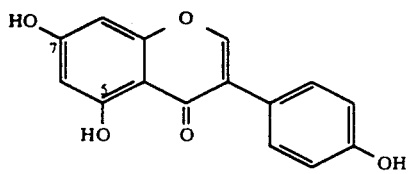

If the OH group is in the 5 position, a complex will be formed in the presence of aluminium chloride in accordance with the following reaction:

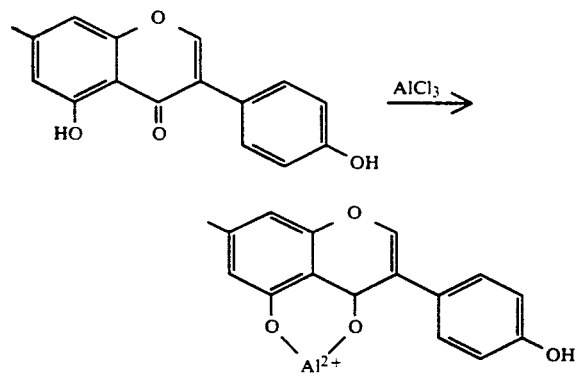

Now, the λmax of the complex thus formed is higher by about 10 to 14 nm than the λmax of the genistin malonate. The λmax of the genistin malonate is measured in methanol optionally in the presence of aluminium chloride. The following results are obtained:

| | |
|---|---|
| without AlCl$_3$ | λmax = 260.1 nm |
| with AlCl$_3$ | λmax = 270.7 nm |

A complex is formed in the presence of aluminium chloride; the free OH group is thus in the 5 position and the sugar group in the 7 position.

ii) Decomposition in Alkaline Medium

The retention time of malonic acid and genistin malonate, as such or in the presence of sodium hydroxide, is measured by high-performance liquid chromatography (HPLC) at 228 nm. The following results are obtained:

Malonic acid
One peak is obtained at 2.19 mins.
Malonic acid + NaOH
Two peaks are obtained: one at 2.19 mins. corresponding to malonic acid and one at 5.08 mins. corresponding to sodium malonate.
Genistin malonate
One peak is obtained at 15.17 mins.
Genistin malonate + NaOH
Two peaks are obtained: one at 12.80 mins. corresponding to genistin and one at 5.07 mins. corresponding to sodium malonate.

The genistin malonate is thus decomposed in the presence of sodium hydroxide into sodium malonate and genistin.

iii) Infra-Red Spectrum

The IR spectrum of genistin malonate in the solid state in a concentration of 1% in KBr shows a characteristic band at 1729.2 cm$^{-1}$ corresponding to the carbonyl group of the ester (theoretical value 1735±10 cm$^{-1}$).

iv) Mass Spectrum

Mass spectrum was prepared by two methods giving a result by deficiency ("negative FAB") and a result by excess ("positive FAB").

The following results are obtained:
A: molecular peak of the compound (genistin malonate)
B: peak corresponding to isoflavone glucoside (genistin)
C: peak corresponding to the basic aglycone (genistein)

Genistin Malonate (Molecular Weight, g)

| | Negative FAB | Positive FAB | Theoretical value |
|---|---|---|---|
| A | 517 | 519 | 518 |
| B | 431 | 433 | 432 |
| C | 269 | 271 | 270 | v) NMR Spectrum

The 13C nuclear magnetic resonance spectrum (NMR) of genistin malonate in dimethyl sulfoxide (DMSO-d6) at 20° C. shows the following characteristic signals:

| Signal | Multiplicity |
|---|---|
| 45,4 ppm | CH$_2$ |
| 63,1 ppm | CH$_2$ |
| 69,7 ppm | CH |
| 73,0 ppm | CH |
| 74,0 ppm | CH |
| 76,0 ppm | CH |
| 94,3 ppm | CH |
| 99,4 ppm | CH |
| 99,7 ppm | CH |
| 106,3 ppm | C |
| 115,0 ppm | CH (2 carbons) |
| 120,8 ppm | C |
| 122,6 ppm | C |
| 130,0 ppm | CH (2 carbons) |
| 154,0 ppm | CH |
| 157,2 ppm | C |
| 157,7 ppm | C |
| 161,7 ppm | C |

| Signal | Multiplicity |
|---|---|
| 162.5 ppm | C |
| 168.4 ppm | C |
| 169.2 ppm | C |
| 179.9 ppm | C |

Thus, a total of 24 carbons was found, of which 3 are carbonyl carbons (carboxylic acid and conjugated ketone), 14 are aromatic or olefinic (7 CH, 7 quaternary) 5 of the 14 being O-substituted, 1 is an anomeric CH—OH, 4 are O-substituted aliphatic CH, 1 is an O-substituted aliphatic $CH_2$ and 1 is a non-O-substituted aliphatic $CH_2$. 16 non-exchangeable protons were found as well.

IDENTIFICATION TESTS FOR THE DAIDZIN MALONATE i) Decomposition in Alkaline Medium

The retention time of malonic acid and daidzin malonate, as such or in the presence of sodium hydroxide, is measured by high-performance liquid chromatography (HPLC) at 228 nm. The following results are obtained:

Malonic acid
one peak is obtained at 2.19 mins.
Malonic acid + NaOH
two peaks are obtained: one at 2.19 mins. corresponding to malonic acid and one at 5.08 mins corresponding to sodium malonate.
Daidzine + NaOH
one peak is obtained at 8.66 mins.
Daidzin malonate
one peak is obtained at 13.89 mins.
Daidzin malonate + NaOH
is obtained:
a) immediately after the mixing, one peak at 11.47 mins. corresponding to daidzin and one peak at 8.65 mins. corresponding to the one obtained for the daidzin + NaOH
b) after 1 hour, one peak at 8.65 mins. corresponding to the one obtained for daidzin + NaOH.

ii) Infra-Red Spectrum

The IR spectrum of daidzin malonate in the solid state in a concentration of 1% in KBr shows a characteristic band at 1734.0 cm$^{-1}$ corresponding to the carbonyl group of the ester. (theoretical value 1735±10 cm$^{-1}$).

iii) Mass Spectrum

Mass spectrum was prepared by two methods giving a result by deficiency and a result by excess. The following results are obtained:
A : molecular peak of the compound (daidzin malonate)
B : peak corresponding to isoflavone glucoside (daidzin)
C : peak corresponding to the basic aglycone (daidzein)

Daidzin Malonate (Molecular Weight, g)

| | Negative FAB | Positive FAB | Theoretical value |
|---|---|---|---|
| A | 501 | 503 | 502 |
| B | 415 | 417 | 416 |
| C | 253 | 255 | 254 | iv) NMR Spectrum

The 13C nuclear magnetic resonance spectrum (NMR) of daidzin malonate in dimethyl sulfoxide (DMSO-d6) at 20° C. shows the following characteristic signals:

| Signal | Multiplicity |
|---|---|
| 45,2 ppm | $CH_2$ |
| 63,0 ppm | $CH_2$ |
| 69,7 ppm | CH |
| 73,0 ppm | CH |
| 74,0 ppm | CH |
| 76,1 ppm | CH |
| 99,7 ppm | CH |
| 103,4 ppm | CH |
| 114,9 ppm | CH (2 carbons) |
| 115,3 ppm | CH |
| 118,4 ppm | C |
| 122,0 ppm | C |
| 123,6 ppm | C |
| 126,9 ppm | CH |
| 129,9 ppm | CH (2 carbons) |
| 153,2 ppm | CH |
| 156,8 ppm | C |
| 157,4 ppm | C |
| 161,0 ppm | C |
| 168,3 ppm | C |
| 169,1 ppm | C |
| 174,7 ppm | C |

Thus, a total of 24 carbons was found, of which 3 are carbonyl carbons (carboxylic acid and conjugated ketone), 14 are aromatic or olefinic (8 CH, 6 quaternary) 4 of the 14 being O-substituted, 1 is an anomeric CH—OH, 4 are O-substituted aliphatic CH, 1 is an O-substituted aliphatic $CH_2$ and 1 is a non O-substituted aliphatic $CH_2$. 17 non-exchangeable protons were found as well.

ACTIVITY TESTS FOR THE COMPOUNDS i) Qualitative Analysis

It is known that $\beta$-carotene is oxidized in the presence of linoleic acid by ultraviolet (UV) irradiation. The oxidation is reflected in the decolouration of the $\beta$-carotene.

One drop of an aqueous solution of daidzin, genistin, daidzin malonate or genistin malonate is applied to a support plate for thin-layer chromatography. A solution containing 100 mg $\beta$-carotene and 1 ml linoleic acid in 100 ml chloroform is then vaporized on the plate. The plate turns yellow. The plate is placed beneath a UV light source and left there until decolouration occurs. It can be seen that, at the places where the genistin and the daidzin were applied, the plate is not decoloured and is still yellow in colour. This is attributable to the fact that the daidzin and the genistin have antioxidant properties which prevent oxidation and, hence, decolouration of the $\beta$-carotene. It can also be seen that the plate has the same yellow colour at the places where the malonates of genistin and daidzin were applied. Accordingly, these two compounds also exhibit antioxidant properties.

ii) Quantitative Analysis by Spectrophotometry 0.01 M solutions of daidzein, genistein, daidzin, genistin, daidzin malonate and genistin malonate in methanol are prepared.

Several solutions of gallic acid in methanol varying in concentration from 0.2 to 20 gl$^{-1}$ are prepared in exactly the same way as standards.

A solution containing 100 mg $\beta$-carotene, 1 ml linoleic acid and 100 ml chloroform is also prepared as reactant.

First samples containing 20 $\mu$l of the solution to be measured, 60 $\mu$l reactant and 2 ml methanol and second control samples containing 20 $\mu$l of the solution to be measured and 2 ml methanol are prepared.

The absorbtion of the sample in relation to its control sample is measured just after preparation, after which the two samples are exposed to ultraviolet radiation for 12 minutes and their absorption is remeasured. The measures are effectued at 450 nm.

The results obtained for the isoflavones may then be compared with the results obtained for the various solutions of gallic acid, enabling the following equivalences to be defined:

| 0.010M Isoflavone solution | Molar concentration of the gallic acid solution having the same antioxidant power |
|---|---|
| Daidzein | 0.020M |
| Daidzin | 0.022M |
| Daidzin malonate | 0.024M |
| Genistein | 0.028M |
| Genistin | 0.027M |
| Genistin malonate | 0.029M |

It can be seen that the 0.010 M solutions of daidzin or genistin malonate have the same effect as the 0.010 M solutions of daidzin or genistin and the 0.024 M and 0.029 M solutions of gallic acid.

iii) Oxidation Test

The Rancimat accelerated oxidation test is used to determine the induction time of chicken fat stabilized by addition of genistin or daidzin malonate.

The Rancimat test comprises passing air through a reaction tube containing a sample of 5 g fat at 100° C. and measuring the conductivity of the volatile secondary products formed during oxidation and entrained with the stream of air. The induction time is graphically determined from the recorded conductivity/time curve by intersection of the tangent to the curve with the time axis.

The following results are obtained for a chicken fat containing 500 ppm genistin or daidzin malonate or none at all (control).

|  | Induction time (h) |
|---|---|
| Control | 6.95 |
| Genistin malonate 500 ppm | 8.10 |
| Daidzin malonate 500 ppm | 7.68 |

The antioxidant effect of genistin malonate and daidzin malonate is thus clearly confirmed.

We claim:

1. A process for obtaining genistin malonate and daidzin malonate comprising:

extracting ground soya bean with a solvent selected from the group of solvents consisting of methanol and ethanol to obtain an extract;

buffering the extract with an aqueous buffer solution to obtain an aqueous solution having a pH of from 6 to 9;

extracting the buffered aqueous solution with a water-immiscible organic solvent and recovering an aqueous phase therefrom;

acidifying the recovered aqueous phase to a pH of from 2 to 5.4;

extracting the acidified aqueous phase with a water-immiscible organic solvent and recovering an organic phase therefrom;

neutralizing the recovered organic phase to a pH of from 6.8 to 7.2; and separating genistin malonate and daidzin malonate from the neutralized organic phase.

2. A process according to claim 1 wherein the neutralized organic phase is dried to obtain an extract containing genistin malonate and daidzin malonate.

3. A process according to claim 2 further comprising passing the extract over a gel column and eluting and collecting a fraction containing genistin malonate and daidzin malonate.

4. A process according to claim 3 further comprising separating genistin malonate and daidzin malonate from each other.

5. A process according to claim 4 wherein genistin malonate and daidzin malonate are separated from each other by subjecting the fraction containing both malonates to inverse-phase chromatography.

6. A process according to claim 5 wherein the fraction containing both genistin malonate and daidzin malonate is passed through a column containing octadecyl silane groups attached to silica and wherein a 10% aqueous ethanol solution is used as eluent at a rate of 2 ml per minute.

7. A process according to claim 1 wherein the ground soya bean has an average particle diameter of from 0.5 mm to 0.8 mm.

8. A process according to claim 1 wherein the ground soya is mixed with a 70%–90% aqueous methanol solution and the mixture is refluxed with stirring for 50–100 minutes at a temperature of 70°–90° C.

9. A process according to claim 8 further comprising filtering the refluxed mixture, recovering a filtrate, and drying the filtrate to obtain the crude extract.

10. A process according to claim 1 wherein the buffered aqueous solution is extracted with a solvent selected from the group of solvents consisting of butanol and ethyl acetate.

11. A process according to claim 1 wherein the recovered aqueous phase is acidified by adding 5–10 N hydrochloric acid.

12. A process according to claim 1 wherein the acidified aqueous phase is extracted with a solvent selected from the group of solvents consisting of butanol and ethyl acetate.

13. A process according to claim 1 wherein each water-immiscible organic solvent is butanol.

14. A process according to claim 1 wherein the ground soya bean is defatted before extraction and separation of the malonates.

15. A process according to claim 14 wherein ground soya beans are mixed with an organic solvent to obtain a mixture, the mixture is refluxed for 50–70 minutes at a temperature of 60°–70° C., the refluxed mixture is cooled and filtered and the ground material is then washed and dried.

16. A method for inhibiting oxidation of a food comprising adding to a food an effective amount of at least one member selected from the group consisting of genistin malonate and daidzin malonate.

17. A method according to claim 16 wherein both genistin malonate and daidzin malonate are added to the food.

18. A method for inhibiting oxidation of a cosmetic comprising adding to a cosmetic an amount of at least one member selected from the group consisting of genistin malonate and daidzin malonate.

19. A method according to claim 18 wherein both genistin malonate and daidzin malonate are added to the cosmetic.

* * * * *

UNITED STATES PATENT AND TRADEMARK OFFICE
CERTIFICATE OF CORRECTION

PATENT NO. : 5,141,746

DATED : August 25, 1992

INVENTOR(S) : Yvette FLEURY, et al.

It is certified that error appears in the above-identified patent and that said Letters Patent is hereby corrected as shown below:

On the title page, under the heading, "References Cited (item [56]), the following references also should be listed:

OTHER PUBLICATIONS

Derwent Abstract, J01146894, DW8929 "New aldose reductase inhibitor-VIZ 6-malonyl-beta D-gluco-pyranosyl-oxy 3-(4-hydroxyphenyl)LIH 1-benzo-pyranone-4".

Francis, C.M., "The influence of Isoflavone Glycosides on the Taste of Subterranean Clover Leaves." J. Sci. Fd. Agric., 1973. 24, 1235-1240.

63-Pharmaceuticals. Vol. 112 (1990), 112:42557y "Isolation of 7-(6-O-malonyl- -D-glucopyranosyl=oxy)-3-(4-hydroxyphenyl)-4H-1-benzopyran-4-one form Pueraria lobata Ohwi as aldose reductase inhibitors and pharmaceutical formulations.

Signed and Sealed this

Seventh Day of September, 1993

Attest:

BRUCE LEHMAN

*Attesting Officer*  *Commissioner of Patents and Trademarks*